(12) United States Patent
Weiss et al.

(10) Patent No.: US 7,772,439 B2
(45) Date of Patent: Aug. 10, 2010

(54) AMINO OR THIOL LINKER BUILDING BLOCK FOR THE SYNTHESIS OF AMINO- OR THIOL-FUNCTIONALIZED NUCLEIC ACIDS AND METHODS OF MAKING AND USE THEREOF

(75) Inventors: Patrick A. Weiss, Huntsville, AL (US); Violette Y. Weiss, Huntsville, AL (US); Stefan Pitsch, Lausanne (CH)

(73) Assignee: Operon Biotechnologies, Inc., Huntsville, AL (US)

( * ) Notice: Subject to any disclaimer, the term of this patent is extended or adjusted under 35 U.S.C. 154(b) by 819 days.

(21) Appl. No.: 11/257,752

(22) Filed: Oct. 25, 2005

(65) Prior Publication Data

US 2006/0167240 A1    Jul. 27, 2006

Related U.S. Application Data

(60) Provisional application No. 60/621,822, filed on Oct. 25, 2004.

(51) Int. Cl.
*A61K 31/661* (2006.01)
*A61K 31/664* (2006.01)
*C07F 9/141* (2006.01)
*C07F 9/24* (2006.01)

(52) U.S. Cl. ............... 568/15; 514/85; 514/89; 514/91; 514/112; 514/124

(58) Field of Classification Search ............ None
See application file for complete search history.

(56) References Cited

U.S. PATENT DOCUMENTS

| 4,725,677 | A | 2/1988 | Koster et al. | |
|---|---|---|---|---|
| 5,864,032 | A * | 1/1999 | Misiura et al. | 536/25.34 |
| 6,211,356 | B1 | 4/2001 | Wiessler et al. | |
| 6,693,187 | B1 | 2/2004 | Dellinger | |
| 7,164,014 | B2 * | 1/2007 | Huang et al. | 536/26.1 |

OTHER PUBLICATIONS

Narayanan et al., "CpG Oligonucleotides with Modified Termini and Nicked Dumbbell Structure Show Enhanced Immunostimulatory Activity" Journal of Medicinal Chemistry (2003) vol. 46 pp. 5031-5044.*

* cited by examiner

*Primary Examiner*—Eric S Olson
(74) *Attorney, Agent, or Firm*—Lanier Ford Shaver & Payne, P.C.; J. Mark Bledsoe

(57) ABSTRACT

An amino or thiol linker building block for the synthesis of amino or thiol functionalized amino acids and generally of the following structure:

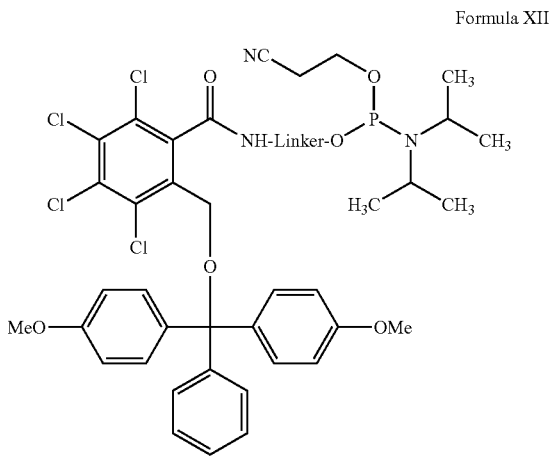

Formula XII is provided. Such building block may be introduced in the 5' end position of an amino acid under standard coupling conditions. Such building block allows in-line coupling control, "trityl-on" purification, and solid support functionalization/derivatization. Such building block is a stable, solid compound and can therefore be easily handled. With the building block of the present invention, deprotection may be carried out under standard detritylation conditions.

7 Claims, No Drawings

AMINO OR THIOL LINKER BUILDING BLOCK FOR THE SYNTHESIS OF AMINO- OR THIOL-FUNCTIONALIZED NUCLEIC ACIDS AND METHODS OF MAKING AND USE THEREOF

CONTINUITY DATA

This invention claims benefit of U.S. provisional application 60/621,822, filed Oct. 25, 2004.

FIELD OF THE INVENTION

This invention generally relates to the field of nucleic acid chemistry. In particular, the present invention relates to an amino or thiol linker building block applicable for the synthesis of amino- or thiol-functionalized nucleic acids (ribo- or deoxyribonucleic acids and derivatives thereof). More particularly, the present invention relates to a method for producing the amino or thiol linker phosphoramidite building block.

BACKGROUND OF THE INVENTION

A common procedure for the chemical synthesis of nucleic acids involves step-wise assembly of suitable, protected phosphoramidite building blocks on solid phase, followed by the removal of protecting groups and the detachment from the solid phase. In addition to the incorporation of ribo- or deoxyribonucleotides, this procedure allows the introduction of other, additional compounds including nucleotide analogs (containing modified sugar moieties and/or modified nucleobase moieties) as well as other molecules which facilitate specific detection and characterization (e.g., dyes) or specific binding (e.g., biotin). The introduction of these compounds into nucleic acids requires the presence of reactive groups and protecting groups that are compatible with the assembly and deprotection protocols employed in the assembly and deprotection of nucleic acids. Ideally, these additional compounds contain a removable reporter/protection group, which allows the in-line monitoring of the coupling efficiency.

The named modifications can only be introduced into nucleic acids if they are stable, both under assembly and deprotection conditions. A variety of very useful and routinely employed dyes and reporter groups are not sufficiently stable and are therefore introduced only after assembly and deprotection of the nucleic acids by so-called conjugation reactions. For their selective and efficient conjugation, an unfunctionalized, reactive, and stable functionality is introduced into the nucleic acid during assembly. The reactive functionalities are usually amino- or thiol-groups. The corresponding building blocks, usually called "amino linkers" or "thiol linkers," respectively, contain typically a phosphoramidite moiety for the attachment to the nucleic acid, a linker chain (alkyl-chains or oligoethylenglycol-chains of various lengths) and the suitably protected reactive amino group or thiol group, respectively.

The reactive amino groups of amino linker building blocks presently known are protected either by a N-trifluoroacetyl-group (Formula I) or by a N-monomethoxytrityl-group (Formula II). Phosphoramidite derivatives of amino linkers containing a primary amino group which is protected as a trifluoroacetyl-derivative (Formula I) can be attached to the 5'-end of a nucleic acid in a usual procedure; after coupling, capping, and oxidation, the still protected amino linker is connected via a phosphoric acid triester moiety to the nucleic acid. The trifluoroacetamido protecting group is then cleaved together with the protecting groups of the nucleobase and the phosphodiester upon treatment of the product with ammonia or methylamine.

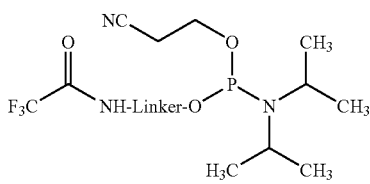

Formula I

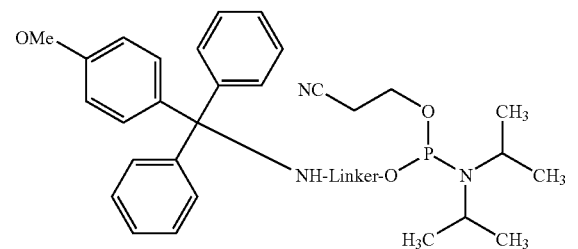

Formula II

N-Trifluoroacetyl-protected amino linkers can be prepared in a simple sequence of reactions from cheap compounds, and their deprotection is very straightforward. Unfortunately, their protecting group cannot be used for controlling coupling efficiency, and neither "trityl-on" purification nor solid support functionalization/derivatization reactions are possible.

Phosphoramidite derivatives of amino linkers comprising a primary amino group which is protected by a monomethoxytrityl group (Formula II) are also attached to a nucleic acid according to the usual procedure, and after capping and oxidation, the monomethoxytrityl protecting group is cleaved under (acidic) detritylation conditions, while the nucleic acid sequence is still attached on the solid support. These formula II monomethoxytrityl-protected amino linkers presented in formula II provide the advantage of simple preparation while allowing for "trityl-on" purification and solid support functionalization/derivatization. Such Formula II amino linkers, however, allow only qualitative control of coupling efficiency and are not completely stable during storage and incorporation into nucleic acids. It is, therefore, desirable to provide an amino or thiol linker building block which is easily produced and stable and which allows control of coupling efficiency, "trityl-on" purification, and solid support functionalization/derivatization.

SUMMARY OF THE INVENTION

The present invention recognizes and addresses various of the foregoing limitations and drawbacks and others concerning amino or thiol linker building block applicable for the synthesis of amino- or thiol-functionalized nucleic acids. Therefore, the present invention is directed to an amino or thiol linker building block and a method for producing each.

It is, therefore, a principle object of the subject invention to provide an amino or thiol linker building block which is easily produced. More particularly, it is an object of the present invention to provide such an amino or thiol linker building block that is stable. In such context, it is still a more particular object of the present invention to provide such an amino or thiol linker building block which allows control of coupling efficiency.

Still further, it is a principle object of this invention to provide an amino or thiol linker building block. It is a further object of the present invention to provide an amino or thiol linker building block which is easily produced, stable, and that allows control of coupling efficiency. In such context, it is an object of the present invention to provide an amino or thiol linker building block that allows for "trityl-on" purification and solid support functionalization/derivatization.

Additional objects and advantages of the invention are set forth in, or will be apparent to those of ordinary skill in the art from, the detailed description as follows. Also, it should be further appreciated that modifications and variations to the specifically illustrated and discussed features and materials hereof may be practiced in various embodiments and uses of this invention without departing from the spirit and scope thereof, by virtue of present reference thereto. Such variations may include, but are not limited to, substitutions of the equivalent means, features, and materials for those shown or discussed, and the functional or positional reversal of various parts, features, method steps, or the like.

Still further, it is to be understood that different embodiments, as well as different presently preferred embodiments, of this invention may include various combinations or configurations of presently disclosed features, elements, method steps, or their equivalents (including combinations of features or configurations thereof not expressly shown in the figures or stated in the detailed description).

These and other features, aspects, and advantages of the present invention will become better understood with reference to the following descriptions and the appended claims. The accompanying drawings, which are incorporated in and constitute a part of this specification, illustrate an embodiment of the invention, and, together with the descriptions, serve to explain the principles of the invention.

In one exemplary embodiment, there may be provided an amino or thiol linker building block with the structure

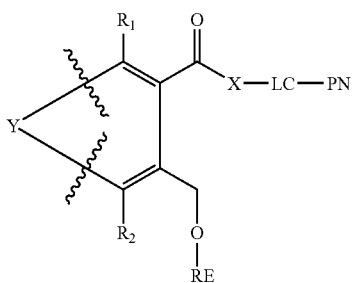

Formula III wherein PN is a suitably protected phosphoramidite moiety, wherein LC is a linker chain (e.g., alkyl- or oligo-ethylenglycol-chain), wherein X is an NH (amino linker) or S (thiol linker) and wherein Y has a structure according to one of the Formulas IV to X. Further, RE is a reporter group (e.g., monomethoxytrityl or dimethoxytrityl), and wherein R1 and R2 are independently halogen or alkyl- or alkyloxy-groups containing one to four C-atoms.

The Y-group of the amino or thiol linker building block according to the present invention has a structure according to one of Formulas IV to X.

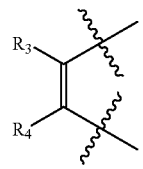

Formula IV

Wherein R3 and R4 ate independently halogen, hydrogen, or alkyl-groups comprising one to four C-atoms, or alkoxy-groups comprising one to four C-atoms.

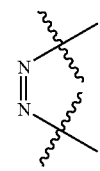

Formula V

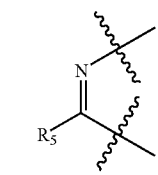

Formula VI

Wherein R5 is hydrogen or an alkyl-group comprising one to four C-atoms.

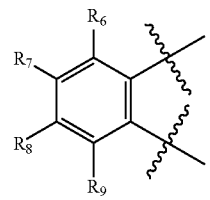

Formula VII

Wherein R6, R7, R8, and R9 are independently halogen, hydrogen or an alkyl-group comprising one to four C-atoms or an alkyloxy-group comprising one to four C-atoms.

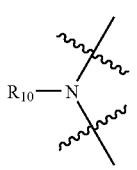

Formula VIII

Wherein R10 is hydrogen or an alkyl-group comprising one to four C-atoms.

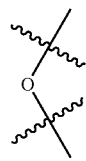

Formula IX

Formula X

The phosphoramidite moiety (PN in Formula III) has the following structure:

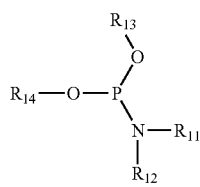

Formula XI wherein R11 and R12 are independently alkyl-groups containing one to four C-atoms, and R13 is a cyanoethyl- or methyl-group, and R14 is the linker chain (as defined in Formula III).

In the building block of the present invention, the amino or thiol group is protected by an amide or thioester bond, and the reporter group is attached to the protecting group by an ether bond, all being stable under basic conditions. On deprotection of the reporter group under acidic conditions (e.g., standard detritylation conditions), first the ether bond and consecutively the amide or thioester bond are cleaved. As a result, the amino or thiol group linker building block according to the present invention is a very stable solid compound and can therefore be easily handled, but upon removal of the reporter group, the amide or thioester bond are spontaneously cleaved.

DETAILED DESCRIPTION OF THE INVENTION

Reference will now be made in detail to a presently preferred embodiment of the invention, examples of which are fully represented in the accompanying formulas. Such examples are provided by way of explanation of the invention, not limitation thereof. In fact, it will be apparent to those skilled in the art various modifications and variations can be made in the present invention without departing from the spirit and scope thereof. For instance, features illustrated or described as part of one embodiment may be used on another embodiment to yield still a further embodiment. Still further, variations and selections of chemicals or materials and/or characteristics may be practiced to satisfy particular desired user criteria. Thus, it is intended that the present invention cover such modifications and variations as come within the scope of the present features and their equivalents.

One exemplary embodiment of an amino or thiol linker building block according to the present invention has a chemical structure according to Formula XII.

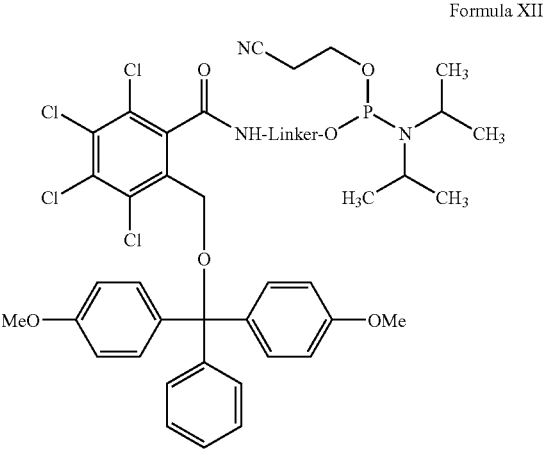

Formula XII

In the amino linker building block according to Formula XII, the amino group is protected by a 3,4,5,6-tetrachloro-2-[(dimethoxytrityl)oxymethyl]benzoyl group. The amino group is thereby linked via a stable amide bond to the protecting group. Upon removable of the dimethoxytrityl group under standard acidic conditions, this amide bond is attacked by the liberated HO-group, thereby forming a lactone and liberating the amino group. Such reaction can be carried out, either on a synthesizer or in the course of a "trityl-on" purification.

Coupling of the exemplary amino linker building block according to Formula XII to a nucleic acid and its deprotection are realized according to the following disclosed methodology:

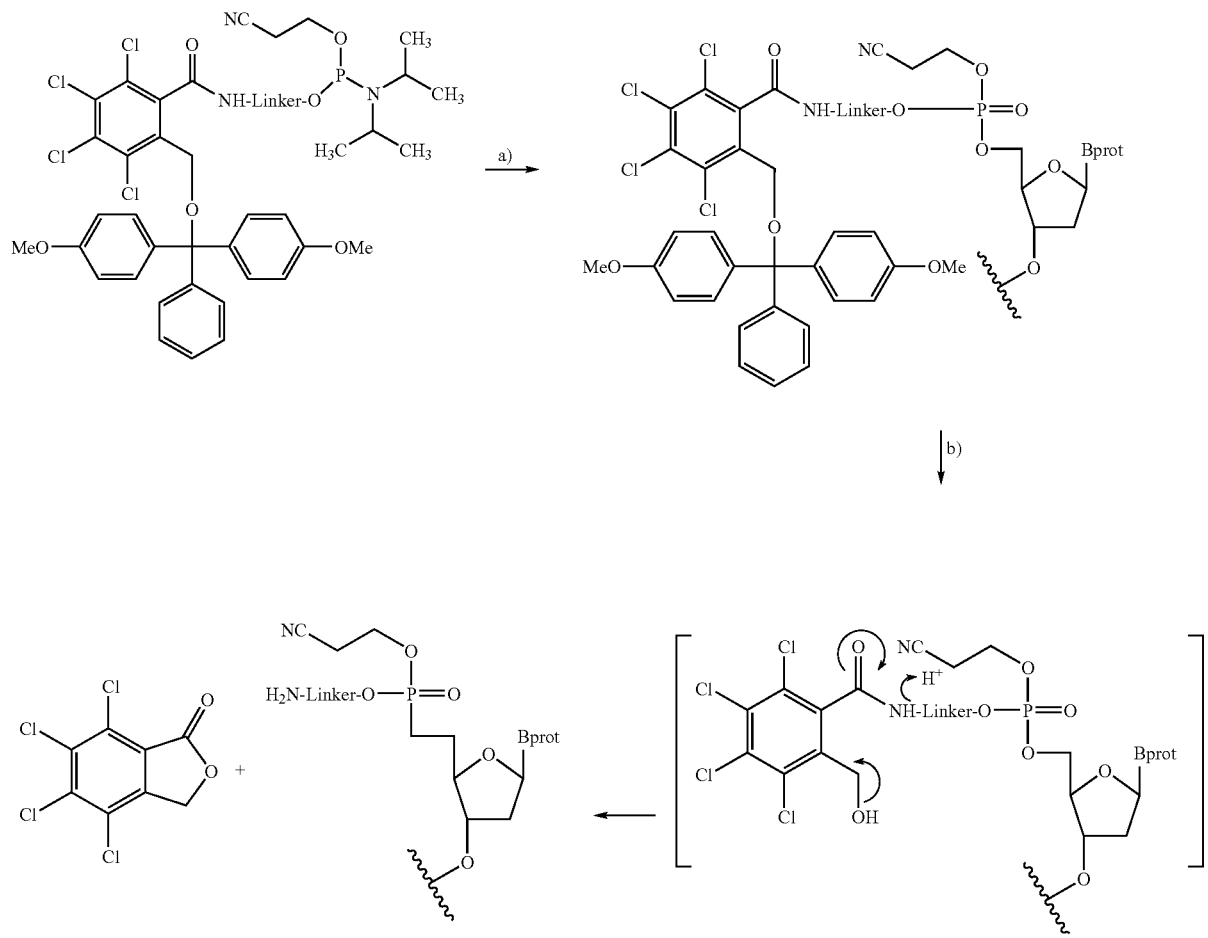

wherein step A is a coupling step on a nucleic acid synthesizer under standard conditions (coupling, capping, oxidation reaction), and step B is a deprotecting step under detritylation conditions (e.g., 3% dichloracetic acid in dichloroethane).

Synthesis of the present exemplary embodiment of an amino or thiol linker building block according to the present invention may start from the cyclic anhydride of a suitable substituted benzene 1,2-dicarboxylic acid (e.g., a substituted phthalic anhydride) which is reduced to a cyclic ester. The ester may then be hydrolized under basic conditions. The hydroxy group of the hydrolized ester is reacted with the reporter group (e.g., dimethoxytrityl chloride). The carboxy group of the hydrolized ester is turned into an amide group or thioester group by reaction with a linker unit comprising the linker chain carrying at its one end the amino or thiol group and at the other end a hydroxy group. The hydroxy group of the linker chain is finally phosphitylated.

The below methodology depicts the synthesis of the present exemplary embodiment of the amino linker building block according to Formula XII and in accordance with the present invention.

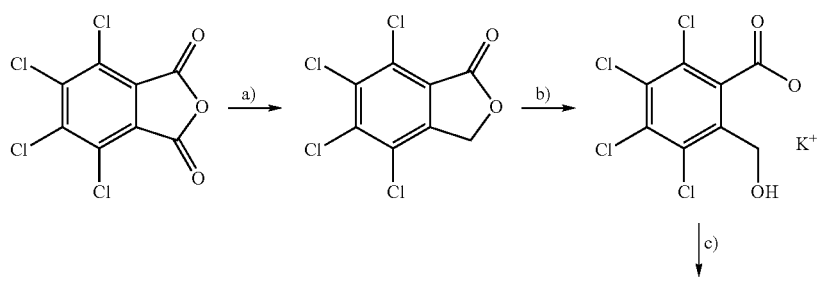

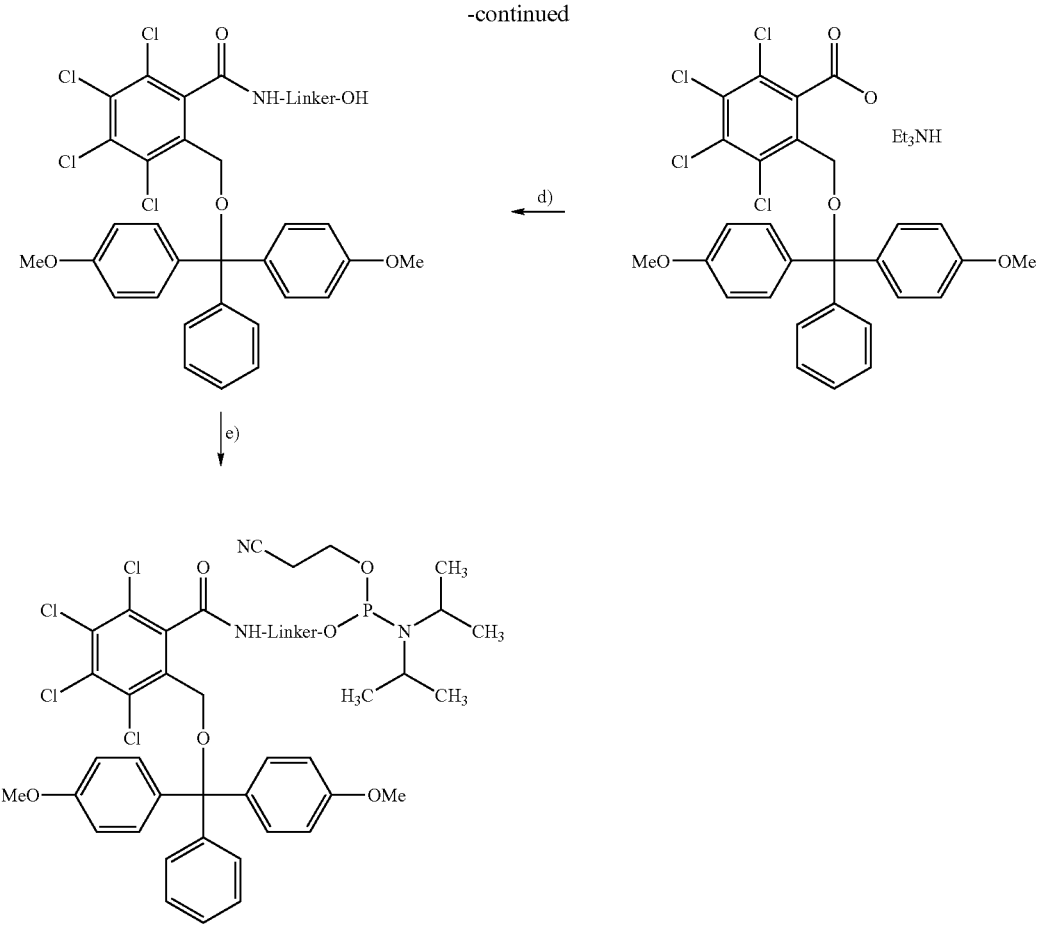

wherein step A is the reduction of the cyclic anhydride with LiBH$_4$ in THF, step B is the hydrolysis of the ester with KOH in MeOH/H$_2$O, step C is the tritylation step with dimethoxytrityl chloride and Et$_3$N in DMF/pyridine, step D is the step of amide formation with the H$_2$N-linker-OH and BOP in CH$_2$Cl$_2$, and step E is the phosphitylation in CH$_2$Cl$_2$.

Although a preferred embodiment of the invention has been described using specific terms and devices, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of various other embodiments may be interchanged both in whole or in part. Therefore, the spirit and scope of the appended claims should not be limited to the description of the preferred version contained herein.

What is claimed is:

1. An amino or thiol linker building block comprising:
   a) a linker chain;
   b) a phosphoramidite moiety bonded to the linker chain having the structure

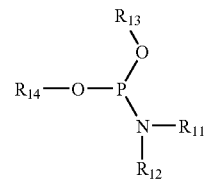

wherein,
   R11 and R12 are independent alkyl-groups containing one to four C-atoms;
   R13 is a methyl-group or cyanoethyl-group; and
   R14 is said linker chain;
c) a protecting group bonded to the linker chain; and
d) a reporter group bonded to the protecting group;
wherein said linker chain (R14) is an alkyl-chain;
wherein said protecting group has the structure

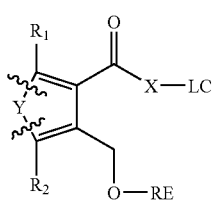

wherein,
X is NH or S;
R1 and R2 are independently halogen, an alkyl-, or an alkyloxy-group containing one to four C-atoms,
LC is the point of attachment to the linker chain,
RE is the point of attachment to the reporter group, and wherein Y is selected from the group comprising:

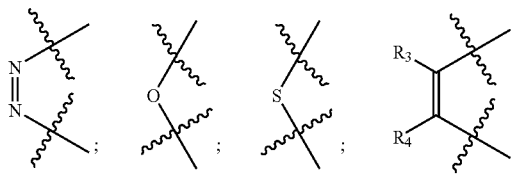

wherein R3 and R4 are independently halogen, hydrogen, or an alkyl-group comprising one to four C-atoms, or an alkyloxy-group comprising one to four C-atoms;

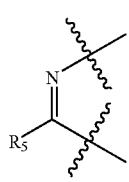

wherein R5 is hydrogen or an alkyl-group comprising one to four C-atoms:

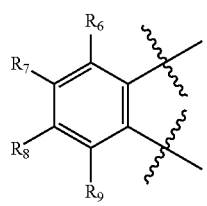

wherein R6, R7, R8, and R9 are independently halogen, hydrogen or alkyl-groups comprising one to four C-atoms, or an alkyloxy-group comprising one to four C-atoms; and

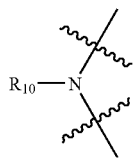

wherein R10 is hydrogen or an alkyl-group comprising one to four C-atoms.

2. An amino or thiol linker building block comprising:
a) a linker chain;
b) a phosphoramidite moiety bonded to the linker chain having the structure

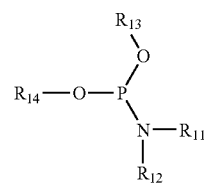

wherein,
R11 and R12 are independent alkyl-groups containing one to four C-atoms;
R13 is a methyl-group or cyanoethyl-group; and
R14 is said linker chain;
c) a protecting group bonded to the linker chain; and
d) a reporter group bonded to the protecting group;
wherein said linker chain (R14) is an oligo-ethyleneglycol;
wherein said protecting group has the structure

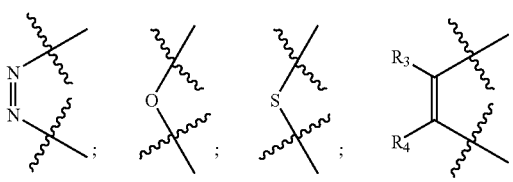

wherein,
X is NH or S;
R1 and R2 are independently halogen, an alkyl-, or an alkyloxy-group containing one to four C-atoms,
LC is the point of attachment to the linker chain,
RE is the point of attachment to the reporter group,
and wherein Y is selected from the group comprising:

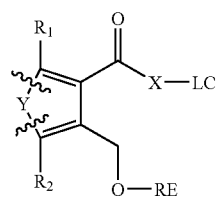

wherein R3 and R4 are independently halogen, hydrogen, or an alkyl-group comprising one to four C-atoms, or an alkyloxy-group comprising one to four C-atoms;

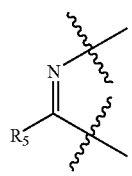

wherein R5 is hydrogen or an alkyl-group comprising one to four C-atoms:

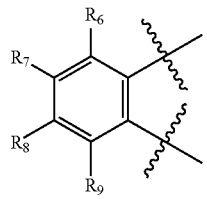

wherein R6, R7, R8, and R9 are independently halogen, hydrogen or alkyl-groups comprising one to four C-atoms, or an alkyloxy-group comprising one to four C-atoms; and

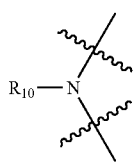

wherein R10 is hydrogen or an alkyl-group comprising one to four C-atoms.

3. An amino or thiol linker building block having the structure

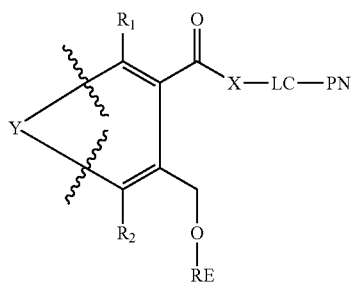

wherein,
  X is NH or
  LC is a linker chain; and
  PN is a phosphoramidite moiety;
RE is a reporter group; and
wherein the remaining structure is a protecting group in which R1 and R2 are independently halogen, an alkyl-, or an alkyloxy-group containing one to four C-atoms; and
wherein Y is selected from the group comprising:

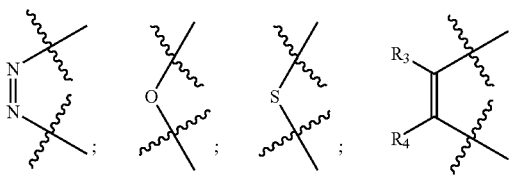

wherein R3 and R4 are independently halogen, hydrogen, or an alkyl-group comprising one to four C-atoms, or an alkyloxy-group comprising one to four C-atoms;

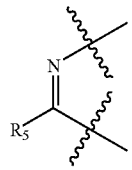

wherein R5 is hydrogen or an alkyl-group comprising one to four C-atoms;

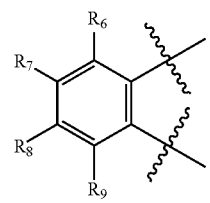

wherein R6, R7, R8, and R9 are independently halogen, hydrogen or alkyl-groups comprising one to four C-atoms, or an alkyloxy-group comprising one to four C-atoms; and

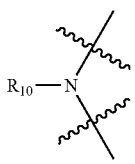

wherein R10 is hydrogen or an alkyl-group comprising one to four C-atoms.

4. The amino or thiol linker building block of claim 3, wherein said phosphoramidite moiety has the structure

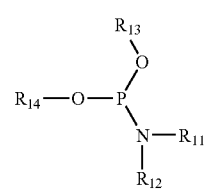

and wherein,
  R11 and R12 are independent alkyl-groups containing one to four C-atoms;
  R13 is a methyl-group or cyanoethyl-group; and
  R14 is said linker chain.

5. The amino or thiol linker building block of claim 4, wherein said linker chain (R14) is an alkyl-chain.

6. The amino or thiol linker building block of claim 4, wherein said linker chain (R14) is a oligo-ethylenglycol chain.

7. An amino or thiol linker building block suited for the synthesis of amino or thiol functionalized amino acids having the general structure

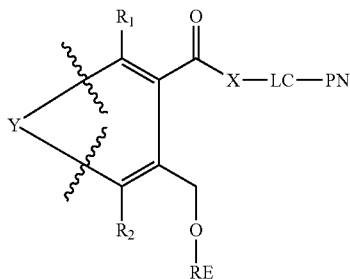

wherein,
X is NH or S;
LC is a linker chain;
PN is a phosphoramidite moiety; and
RE is a reporter group;
wherein the remaining structure is a protecting group in which Ri and R2 are independently halogen, an alkyl-, or an alkyloxy-group containing one to four C-atoms,
Y is selected from the group comprising:

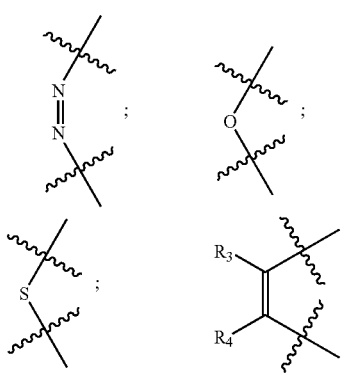

wherein R3 and R4 are independently halogen, hydrogen, or an alkyl-group comprising one to four C-atoms, or an alkyloxy-group comprising one to four C-atoms;

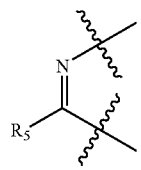

wherein R5 is hydrogen or an alkyl-group comprising one to four C-atoms:

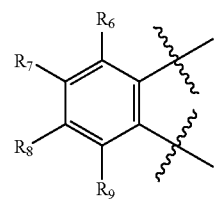

wherein R6, R7, RS, and R9 are independently halogen, hydrogen or alkyl-groups comprising one to four C-atoms, or an alkyloxy-group comprising one to four C-atoms; and

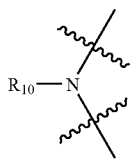

wherein R10 is hydrogen or an alkyl-group comprising one to four C-atoms:

and wherein said linker building block is connected at the 5' end position of an amino acid.

* * * * *